US005543292A

United States Patent [19]
Imai et al.

[11] Patent Number: 5,543,292
[45] Date of Patent: Aug. 6, 1996

[54] PROCESS FOR THE MEASUREMENT OF NUCLEIC ACIDS

[75] Inventors: Kyoko Imai; Kazumichi Imai, both of Katsuta; Yasushi Nomura, Mito, all of Japan

[73] Assignee: Hitachi, Ltd., Tokyo, Japan

[21] Appl. No.: 76,165

[22] Filed: Jun. 14, 1993

[30] Foreign Application Priority Data

Jun. 16, 1992 [JP] Japan .................................. 4-156442

[51] Int. Cl.$^6$ .................................................. C12Q 1/68
[52] U.S. Cl. ........................................................ 435/6
[58] Field of Search .................................. 435/6; 935/77, 935/78

[56] References Cited

U.S. PATENT DOCUMENTS

| | | | |
|---|---|---|---|
| 4,563,419 | 1/1986 | Ranki et al. ................................. | 435/6 |
| 4,775,619 | 10/1988 | Urdea ........................................... | 435/6 |
| 4,797,355 | 1/1989 | Stabinsky ..................................... | 435/6 |
| 4,868,104 | 9/1989 | Kurn et al. ................................... | 435/6 |
| 4,868,105 | 9/1989 | Urdea et al. ................................. | 435/6 |
| 5,118,605 | 6/1992 | Urdea ........................................... | 435/6 |

FOREIGN PATENT DOCUMENTS

| | | |
|---|---|---|
| 3-78120 | 12/1991 | Japan . |
| 5-15439 | 3/1993 | Japan . |

OTHER PUBLICATIONS

Virtanen, the Lancet p. 381–383 (1983) "Novel Test For Rapid Viral Diagnosis: Detection . . . ".
Matthews et al, "Review: Analytical Strategies for the Use of DNA Probes", Analytical Biochemistry, 169, 1988, pp. 1–25.
E. M. Southern, J. Mol. Biol., 98, 503–517, (1975).
J. Meinkoth, Anal. Biochem., 138, 267–284, (1984).

Primary Examiner—W. Gary Jones
Assistant Examiner—Eggerton Campbell
Attorney, Agent, or Firm—Fay, Sharpe, Beall, Fagan, Minnich & McKee

[57] ABSTRACT

A process for detecting the existence of at least one sequence of oligonucleotide in a nucleic acid sample includes at least one performance of a step of mixing the sample with a labeled common polynucleotide, and a polynucleotide probe comprising a sequence complementary to at least a part of the sequence of oligonucleotide and a sequence complementary to at least a part of the labeled common polynucleotide. The existence of a sequence of oligonucleotide which is an analyte existing in a nucleic acid sample can be detected by the use of a common reagent and an unattached polynucleotide having a base sequence specific for the analyte to be measured.

13 Claims, 2 Drawing Sheets

PROCESS FOR THE MEASUREMENT OF NUCLEIC ACIDS

BACKGROUND OF THE INVENTION

1. Field of the Invention

The present invention relates to detection of the existence of a specified sequence of oligonucleotide which is an interesting analyte existing in a nucleic acid sample. The present invention is effective particularly in detection of pathogenic microorganisms such as infectious bacteria and is used for diagnoses and screenings of infectious diseases.

2. Description of the Related Art

Detection and identification of pathogenic microorganisms are indispensable for diagnoses of infectious diseases. Therefore, the antibody titer of the serum of a patient is measured for the specific antigen of a specified pathogenic microorganism. Such a measurement, however, is a mere detection of the shadow of the infectious diseases and is not confirmation of their essence. Detection and identification by cultivation of a microorganism responsible for an infectious disease has been disadvantageous in that it requires a long period of time and hence cannot be employed for practical diagnosis and treatment of the disease.

Investigation of the existence of a specified base sequence in a nucleic acid sample permits specification of a microorganism responsible for an infectious disease and diagnosis of the infectious disease before crisis.

For example, there is a method using a DNA probe. In this method, a single-stranded DNA having a base sequence complementary to the base sequence of a nucleic acid to be detected (the single-stranded DNA is referred to as a "DNA probe") is utilized as a specifically reactive reagent. The existence of objective pathogenic bacteria can be judged by investigating the existence, in a sample, of a base sequence complementary to the base sequence of the DNA probe (E. M. Southern, J. Mol. Biol., 98, 503–517 (1975) and J. Meinkoth, Anal. Biochem., 138, 267–284 (1984)).

As an example of the method using the DNA probe, dot hybridization comprises attaching a single-stranded DNA (an SS-DNA) obtained by denaturation of a sample to a solid phase, allowing a radioisotope-labeled SS-DNA to act on the solid phase to form a hybrid between the labeled SS-DNA and the SS-DNA attached to the solid phase, removing the unreacted labeled SS-DNA, and measuring radiation emitted from the solid phase.

As a modification of the above method, there is sandwich hybridization. This method makes it possible to reduce the background due to adsorption and hence is effective particularly when an impure sample is used. In this method, at least two DNA fragments derived from a target nucleic acid to be recognized are used. One of the DNA fragments is attached to a solid phase and used as a capturing reagent. The other fragment is labeled as a reagent for detection and added to a hybridizing solution together with a solubilized reference sample. When a base sequence homologous with both reagents exists in the reference sample, the sequence ought to be hybridized with both the capturing reagent and the reagent for detection. Whether the sequence has been hybridized or not can be known through labeling of the solid phase.

The above two methods are disadvantageous particularly when the amount of a nucleic acid to be detected is small. In addition, they have been disadvantageous from the viewpoint of labor and time required for operations because a large number of steps are necessary for measurement and a long time is required, particularly for immobilizing a sample.

A method capable of solving the above problems has been proposed, for example, in Japanese Patent Application Kokoku No. 3-78120. This method uses a restriction enzyme. It comprises bringing, in a solution, a single-stranded polynucleotide to be measured into contact with a solid phase to which a labeling substance, a single-stranded polynucleotide to be measured and a double-stranded polynucleotide have been attached, thereby forming a double-stranded polynucleotide; allowing a restriction enzyme to cleave the formed double-stranded polynucleotide and measuring the labeling substance in the solution or solid phase.

U.S. Pat. No. 5,118,605 discloses a method using a restriction enzyme or a reagent having an optional cleavage position introduced thereinto.

In the measurement of nucleic acids by the use of DNA probes, reagents containing different respective DNA probes should be prepared for different analytes to be measured (i.e. sequences of oligonucleotide which are interesting analytes existing in nucleic acid samples). Since the development of the DNA probes requires a great deal of labor, the development of the reagents for the measurement tends to be retarded. This has been a cause of the retardation of generalization of a method for detecting infectious bacteria by investigating the existence of a specified sequence of oligonucleotide, which is an interesting analyte existing in a nucleic acid sample.

In reducing measurement errors due to nonspecific adsorption or the like, a method comprising recognition of a double strand formed by combination and selective cleavage is also effective. However, analysis using different DNA probes for different analytes to be measured requires recognition of the double strand by different restriction enzymes for the different analytes to be measured and selective cleavage of the double strand. Therefore, for developing reagents for measurement, it has been necessary to compose a measuring kit by preparing the different restriction enzymes for the different analytes to be measured. Since a great deal of labor is required for developing a restriction enzyme capable of recognizing a special sequence of oligonucleotide (a specified base sequence) and cleaving the same selectively, the development of the reagents for measurement tends to be retarded and moreover only very expensive restriction enzymes have been developed. This has been another cause of the retardation of generalization of a method for detecting infectious bacteria by investigating the existence of a specified sequence of oligonucleotide which is an interesting analyte.

Thus, in the conventional methods, reagents quite separately developed should be prepared for analytes to be measured, respectively.

SUMMARY OF THE INVENTION

The present invention relates to a process for detecting the existence of at least one sequence of oligonucleotide in a nucleic acid sample which comprises at least one peformance of a step of mixing said sample with a labeled common polynucleotide, and a polynucleotide probe comprising a sequence complementary to at least a part of said sequence of oligonucleotide and a sequence complementary to at least a part of said labeled common polynucleotide.

The present invention relates also to a process according to the above, wherein, referring to FIG. 1A, said nucleic acid sample(S) is mixed with a labeled common first polynucleotide (1) and a second polynucleotide (2) as a probe which comprises a sequence complementary to at least a part of said sequence of oligonucleotide and a sequence complementary to at least a part of the first polynucleotide.

The present invention relates also to a process according to the above, wherein, referring to FIG. 1B, said nucleic acid sample(S) is mixed with a labeled common first polynucleotide (1); a second polynucleotide (2) as a probe which comprises a sequence complementary to at least a part of said sequence of oligonucleotide and a sequence complementary to at least a part of the first polynucleotide; a common third polynucleotide (3) attached to a solid phase; and a fourth polynucleotide (4) as a probe which comprises a sequence complementary to at least a part of said sequence of oligonucleotide and a sequence complementary to at least a part of the common third polynucleotide attached to the solid phase.

The present invention relates also to a process according to the above, wherein, referring to FIG. 1C, a plurality of sequences of oligonucleotide exist as analytes in said nucleic acid sample; for detecting the existence of a first sequence of oligonucleotide (S1), said nucleic acid sample is mixed with a labeled common first polynucleotide (1) and a second polynucleotide (2) as a probe which comprises a sequence complementary to at least a part of said first sequence of oligonucleotide and a sequence complementary to at least a part of the first polynucleotide; and for detecting the existence of a second sequence of oligonucleotide (S2), said nucleic acid sample is mixed with the labeled common first polynucleotide (1) and a third polynucleotide (3) as a probe which comprises a sequence complementary to at least a part of said second sequence of oligonucleotide and a sequence complementary to at least a part of the first polynucleotide.

The invention further relates to a process wherein, referring to FIG. 1D, a plurality of sequences of oligonucleotide exist as analytes in said nucleic acid sample; for detecting the existence of a first sequence of oligonucleotide (S1), said nucleic acid sample is mixed with a labeled common first polynucleotide (1), a second polynucleotide (2) as a probe which comprises a sequence complementary to at least a part of said first sequence of oligonucleotide and a sequence complementary to at least a part of the first polynucleotide, a common third polynucleotide (3) attached to a solid phase, and a fourth polynucleotide (4) as a probe which comprises a sequence complementary to at least a part of said first sequence of oligonucleotide to be detected and a sequence complementary to at least a part of the common third polynucleotide attached to the solid phase; and for detecting the existence of a second sequence of oligonucleotide (S2), said nucleic acid sample is mixed with the labeled common first polynucleotide (1), a fifth polynucleotide (5) as a probe which comprises a sequence complementary to at least a part of said second sequence of oligonucleotide and a sequence complementary to at least a part of the first polynucleotide, the common third polynucleotide (3) attached to the solid phase, and a sixth polynucleotide (6) as a probe which comprises a sequence complementary to at least a part of said second sequence of oligonucleotide to be detected and a sequence complementary to at least a part of the common third polynucleotide attached to the solid phase.

The present invention relates also to an apparatus for measuring a nucleic acid which comprises a means for supplying a nucleic acid sample, a means for supplying a labeled common polynucleotide, and at least one means for supplying a polynucleotide probe comprising a sequence complementary to at least a part of a sequence of oligonucleotide which is an analyte and a sequence complementary to at least a part of said labeled common polynucleotide.

According to the present invention, a DNA probe used as a reagent need not be attached directly to a solid phase or a label, unlike in the conventional methods, and it may be attached through a linker. In detail, a common polynucleotide independent of the analyte is attached to a solid phase or a label, and there is used a DNA probe comprising both a base sequence complementary to the common polynucleotide and a base sequence capable of recognizing the base sequence of a nucleic acid which is an analyte. Since the DNA probe is attached to the solid phase or the label through the common polynucleotide at the time of the analytical reaction, there can be obtained a reaction result that is substantially equal to that obtained by the direct attachment conventionally employed. This method permits the common use of reagents and makes unnecessary the conventional preparation of different reagents for different analytes to be measured.

In reducing measurement errors due to nonspecific adsorption or the like, it is effective to involve in the present invention a means for recognizing a double strand formed by combination and cleaving the same selectively. When a DNA probe comprising a common polynucleotide independent of the analyte is linked to a solid phase or a label as described above, employment of a common restriction enzyme independent of the analyte becomes possible. Therefore, to carry out each analysis, it is sufficient that there are prepared a common reagent and an unattached polynucleotide comprising a base sequence specific for an analyte.

DETAILED DESCRIPTION OF THE INVENTION

Figure 1A:
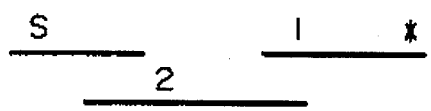
FIG. 1A is a scheme illustrating a particular embodiment of the invention wherein a nucleic acid sample is mixed with a labeled common first polynucleotide and a second polynucleotide as a probe.
Figure 1B:
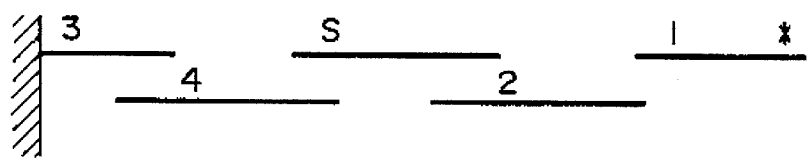
FIG. 1B is a scheme illustrating another embodiment of the invention wherein a nucleic acid sample is mixed with a labeled common first polynucleotide, a second polynucleotide as a probe, a common third polynucleotide attached to a solid phase, and a fourth polynucleotide as a probe.
Figure 1C:
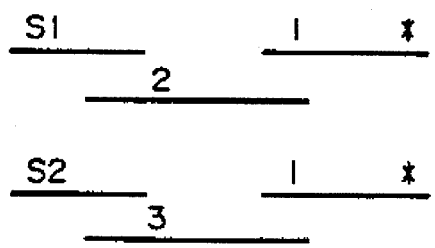
FIG. 1C is a scheme illustrating a further embodiment of the invention wherein a plurality of sequences of oligonucleotides exist as analytes in the nucleic acid sample illustrated in FIG. 1A, with second and third polynucleotides being used as probes for first and second sequences of oligonucleotide, respectively.
Figure 1D:
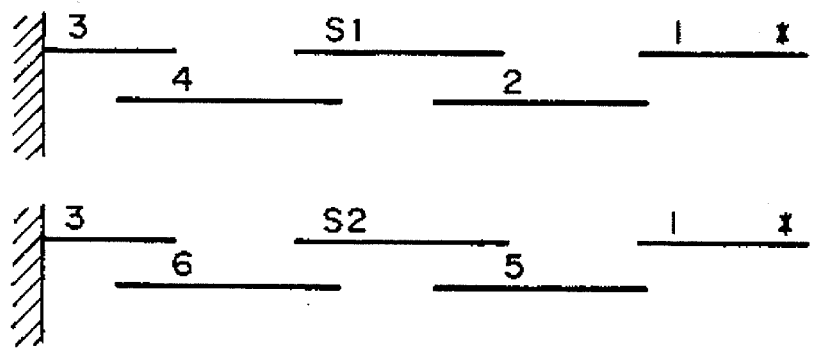
FIG. 1D is a scheme illustrating another embodiment of the invention wherein a plurality of sequences of oligonucleotide exist as analytes in the nucleic acid sample illustrated in FIG. 1B, with second and fourth polynucleotides are used as probes for a first sequence of oligonucleotide, and fifth and sixth polynucleotides are used as probes for a second sequence of oligonucleotide.

A specified sequence is detected on the hybridization principle.

Although in the present invention, a nucleic acid in a sample is preferably in a free state in a solution, it may be attached to a support. It may be in a state in which the base sequence of the nucleic acid that is to be detected is attached to a solid phase through a common polynucleotide reagent attached to the solid state and a polynucleotide reagent.

In a process according to the present invention, for detecting the existence of a sequence of oligonucleotide which is an analyte existing in a nucleic acid sample, the nucleic acid sample is mixed with a labeled first polynucleotide and a second polynucleotide comprising a sequence complementary to the sequence of oligonucleotide to be detected and a sequence complementary to the labeled polynucleotide.

There may be added a step of mixing the nucleic acid sample with a third polynucleotide attached to a solid phase and a fourth polynucleotide comprising a sequence complementary to said sequence of oligonucleotide to be detected and a sequence complementary to the polynucleotide attached to the solid phase. Reactions in this case, for example, are explained below in due order. The order of the reactions in the present invention is not limited to the following order.

1. The third polynucleotide attached to the solid phase is mixed with the fourth polynucleotide.

2. A part of the fourth polynucleotide which is free in a liquid is removed by washing.

3. The residue is reacted with the nucleic acid sample containing the oligonucleotide as an analyte which has been made into single strands., 4. The second polynucleotide is mixed with the reaction mixture.

5. A part of the second polynucleotide which is free in a liquid is removed by washing.

6. The labeled first polynucleotide is reacted with the residue.

7. A part of the labeled first polynucleotide which is free in a liquid is removed by washing.

8. A restriction enzyme capable of recognizing a double-stranded portion and cleaving the same selectively is allowed to act on the residue.

9. A signal derived from a label free in a liquid is detected.

In detail, the labeled first polynucleotide is prepared by attaching a label to a common polynucleotide independent of the analyte. A DNA probe comprising both a base sequence complementary to the common polynucleotide and a base sequence capable of recognizing the base sequence of the oligonucleotide to be detected is used as the second polynucleotide. Since the DNA probe (the second polynucleotide) is linked to the label through the common polynucleotide (the first polynucleotide) at the time of the analytical reaction, there can be obtained a reaction result substantially equal to that obtained when the oligonucleotide to be detected is linked directly to a labeled nucleotide as before.

Similarly, the DNA probe (the fourth polynucleotide) is linked to the solid phase through the common polynucleotide attached to the solid phase (the third polynucleotide). Therefore, there can be obtained a reaction result substantially equal to that obtained when the oligonucleotide to be detected is linked directly to a nucleotide attached to a solid phase, as before.

Since the DNA probes (the second and fourth polynucleotides) are linked to the label or the solid phase, respectively, through the common polynucleotides independent of the analyte, a common restriction enzyme which is often relatively inexpensive can be allowed to act on a double-stranded portion to dissociate or cleave the double-stranded portion, whereby the label attached to the probe can be liberated into a liquid.

In the present invention, the same labels as used in conventional methods can be used. There can be suitably used, for example, fluorescent labels, luminescent labels, enzymes, and fine particles. In general, these labels can be liberated into a liquid by cleavage or dissociation of a double-stranded portion formed by the common polynucleotide and the DNA probe comprising both a base sequence complementary to this common polynucleotide and a base sequence capable of recognizing the base sequence of the oligonucleotide which is an analyte. Therefore, the amount of a signal derived from the label liberated into the liquid is proportional to the amount of the base sequence, i.e., the analyte. The signal derived from the label can be detected by a heretofore known method. When particles are used as the label, a commercially available flow cytometer can be used.

When particles are used as the label, their average particle size is preferably 0.01 to 10 μm, particularly preferably 0.01 to 1.0 μm.

As the particles, there are preferably used fluorescent fine particles or magnetic particles. The fluorescent fine alternatively, particles practically include those which have a fluorescent material layer formed at the surface of latex particles or inorganic material particles, those which are obtained by granulating a mixture of a fluorescent material and a composition for granulation, gels such as sephadex, ion-exchange resins and the like.

When the fluorescent microparticles are used as the label, a flow cytometer may be preferably used to measure the emitted fluorescence from the fine particles. The flow cytometer detects the fluorescence and counts the number of particles passing through a flow cell.

The fluorescent material for the fine particles includes fluorescein, coumarin derivatives, rhodamine derivatives, umbelliferone and the like, which are well-known.

Alternatively, particles having no fluorescence can be used as the label. In this case the particles are optically counted by measuring the turbidity caused by the particles in terms of a scattering intensity or an optical density.

The size of the polynucleotide used as the DNA probe is usually about 15 bases or more, and preferably 50 bases or more. Usually, a region homologous with the sequence in a nucleic acid sample is present in the polynucleotide. The interesting sequence has at least 6 bases, usually at least 12 bases. The region for hybridization has 16 bases or more and its length is usually not more than about 1000 bases. Although the homology percentage need not be 100%, it is preferably at least about 50%, more preferably at least 80%.

An example is described below for illustrating the present invention in further detail, but it is not intended in any way to limit the scope of the present invention.

EXAMPLE 1

A solution prepared by dissolving a sample containing 1 mg/ml of a double-stranded DNA in 0.14 M NaCl was boiled for 10 minutes and then rapidly cooled with ice to make the double-stranded DNA into single-stranded DNAs. The single-stranded DNA solution thus obtained was diluted with a buffer solution for hybridization, whereby samples for preparing a calibration curve were obtained. As the buffer solution for hybridization, there was used the following solution: 5×SSC, 0.5% BSA, 0.5% PVA and 1% SDS.

A solution of 200 μg/ml of a first single-stranded DNA probe in phosphate buffer (PBS: 0.14 M NaCl, 0.01% phosphate buffer, pH 7.2) was added to a 0.1% polystyrene latex particle A solution (particle size: 0.2 μm) containing a fluorescent dye, and the resulting mixture was incubated at 37° C. for 2 hours. The first single-stranded DNA probe adsorbed on latex particles A is referred to as "reagent 1".

There was prepared a second polynucleotide reagent comprising a sequence complementary to the sequence of oligonucleotide of the single-stranded DNA to be detected and a sequence complementary to the fluorescence-labeled polynucleotide (the first single-stranded DNA probe). This reagent is referred to as "reagent 2".

Next, a third single-stranded DNA probe was added to a micro-titer plate and incubated at 37° C. for 2 hours. The thus-treated micro-titer plate is referred to as "reagent 3".

There was further prepared a fourth polynucleotide reagent comprising a sequence complementary to the sequence of oligonucleotide of the single-stranded DNA to be detected and a sequence complementary to the third polynucleotide attached to the solid phase. This reagent is referred to as "reagent 4".

To the micro-titer plate having the third single-stranded DNA probe immobilized thereon (reagent 3) was added 50 μl of reagent 4, and the temperature was maintained at 65° C. for 3 hours. The excess reagent 4 was removed by washing with PBS. To the thus treated micro-titer plate was added 10 μl of the sample for preparing a calibration curve, and the temperature was maintained at 65° C. for another 3 hours. Interfering components contained in the sample were removed by washing with PBS, after which 50 μl of reagent 2 was added, and the temperature was maintained at 65° C. for another 2 hours. The excess reagent 2 was removed by washing with PBS. Then, 10 μl of reagent 1 was added to the residue. The temperature was maintained at 65° C. for 3 hours, after which the excess reagent 1 was removed by washing with PBS.

Finally, latex particles A attached to the micro-titer plate as a result of the reaction were liberated into a liquid by the action of a restriction enzyme capable of recognizing a double-stranded portion and cleaving the same. The restriction enzyme was selected for its ability to cleave a double strand not by recognition of a base sequence specific for the analyte, but by recognition of a common base sequence portion independent of the analyte.

The liberated latex particles A containing the fluorescent dye were counted by means of a commercially available flow cytometer.

| Calibration curve | |
| --- | --- |
| Double-stranded DNA concentration (μg/ml) | Number of particles (×100) |
| 0 | 1 |
| 1 | 13 |
| 5 | 49 |
| 10 | 103 |
| 50 | 511 |

EXAMPLE 2

An embodiment of the present invention is described below with reference to FIG. 2.

Figure 2:
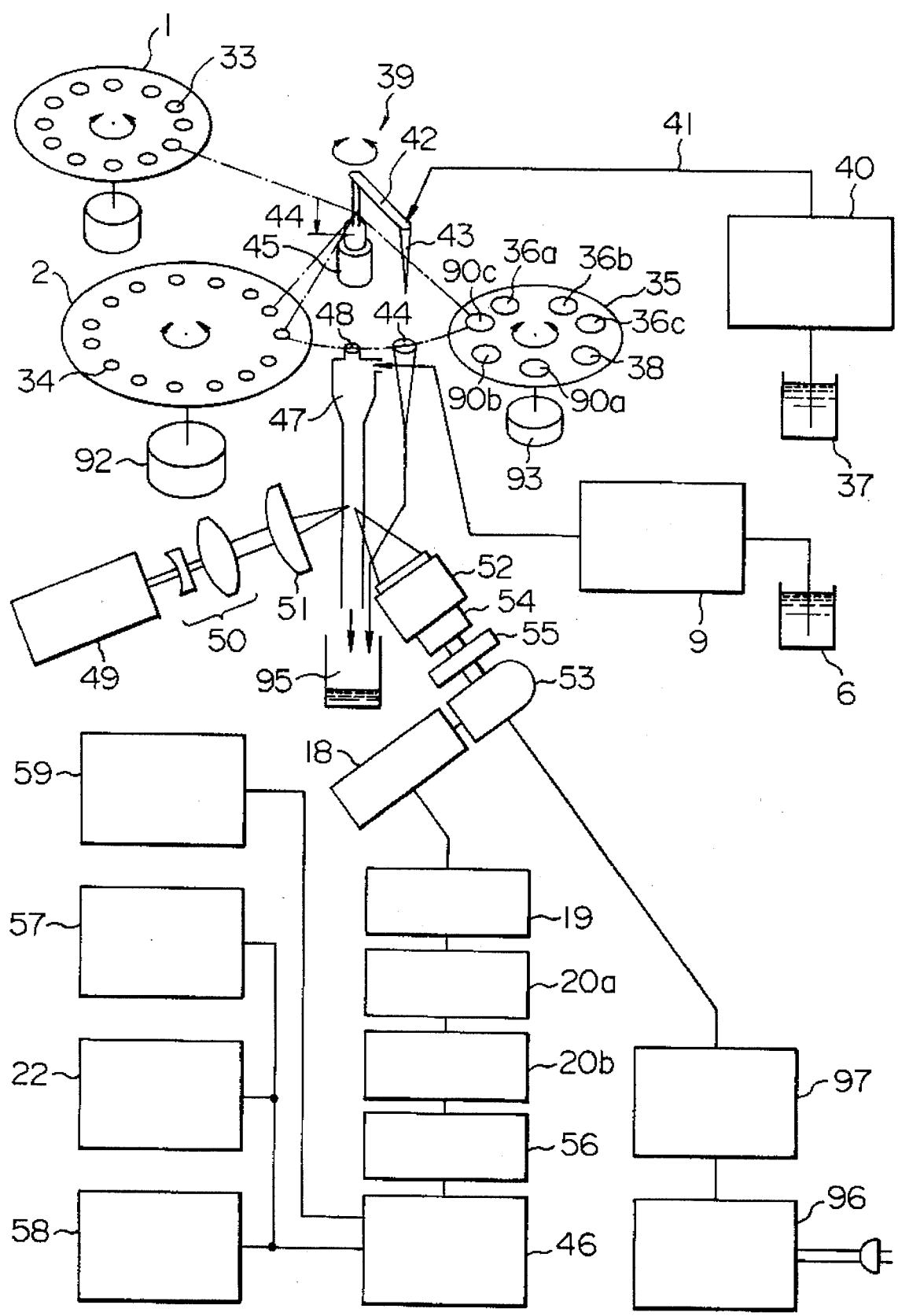
FIG. 2 is a block diagram of an automatic analyzer for analyzing nucleic acids of the present invention.

FIG. 2 is a block diagram showing the entire setup of an automatic analyzer suited for the analyses of nucleic acids in an embodiment of the present invention. On a turntable 1, plural sample containers 33 containing the test samples such as blood are disposed in a circle. On another turntable 2, plural reaction vessels 34 are arranged in a circle in a reaction incubator. Each reaction vessel 34 has a filter set in its upper part and consists of a small chamber having small holes in the wall .and a reaction chamber. A suction device is provided so that the excess labelling particles will be discharged out of the reaction vessel 34 through the small holes in its wall. Each turntable is designed to be turned by a pulse motor 92, whose operation is controlled by a controller 46, so that a desired sample container 33 or reaction vessel 34 will be stopped at the position of suction. Transfer of the sample in each sample container 33 is accomplished by a pipetting nozzle 43. A determined amount of a sample is sucked up by the pipetting nozzle 43 and charged into the reaction vessel 34 which has just been brought to the sample charging position.

Set on a reagent table 35 are the plural containers containing the various reagents assigned for the specific analytical operations. That is, a container of a fluorescent particle-labelled polynucleotide, which is a first reagent commonly used for all of the analytical items A, B, C with a nucleic acid as the object of determination, a container of a polynucleotide bound to the particle solid phase, which is a third reagent commonly used for all of the analytical items A, B, C, containers 90a, 90b, 90c of a second polynucleotide corresponding to the analytical items A, B, C, respectively, containers 36a, 36b, 36c of a fourth polynucleotide corresponding to the analytical items A, B, C, respectively, a restriction enzyme liquid container 38, and containers of a washing fluid and other necessary buffer solutions, are held on the reagent table 35. The pulse motor 93, whose operation is controlled by the controller 46, operates to turn the reagent table 35 through a desired angular distance so that a designated reagent container will be brought to the position of suction by the nozzle 43 at proper timing. In this way, the first reagent can be pipetted into a reaction vessel 34 at the position of pipetting of the first reagent by the nozzle 43. By the same operation, the second reagent can be pipetted into a desired reaction vessel 34 at the position of pipetting of the second reagent by the nozzle 43. Similarly, the third and fourth reagents can be pipetted into the designated reaction vessels 34 at the respective reagent pipetting positions.

The automatic pipetting mechanism 39 comprises the pipetting nozzle 43 secured to a movable arm 42, a driving unit 45 for turning the arm 42 horizontally, a driving unit 44 for moving the arm 42 vertically, a syringe pump 40 connected to the nozzle 43 through a tube 41, and a tank 37 of a washing fluid which is also used as an extruding fluid. The pipetting nozzle 43 is turned in accordance with movement of the arm 42 through an arc connecting the sample sucking position on the turntable 1, the reagent pipetting position on the turntable 2, the inlet 48 of the injection chamber of a flow cell 47 and a nozzle cleaning tank 94, and is capable of ascending or descending at each of said positions.

A membrane filter is provided in the upper part of each reaction vessel 34. The hybridization reaction solution of the sample, the third polynucleotide bound to the particle solid phase, the first polynucleotide labelled with the fluorescent particles and the second and fourth polynucleotides, which were reacted in the reaction chamber of a reaction vessel 34, is injected into the membrane filter portion of said reaction vessel 34 by the pipetting nozzle 43 at the reaction solution pipetting position. At the filter washing position, the suction device is operated to discharge the unreacted fluorescent particle-labelled polynucleotide that is smaller than the filter pore diameter out of the reaction vessel through the small holes in the wall of the small chamber of the reaction vessel 34. Injection of the washing fluid into the filter portion in the reaction vessel 34 by the nozzle 43 and the operation of the suction device are repeated to effect perfect washing of the filter portion. A restriction enzyme solution is pipetted into the washed filter portion of the reaction vessel 34 from the restriction enzyme solution container 38 by the nozzle 43 at the restriction enzyme solution pipetting position. After passage of a predetermined period of time, the suction device is operated at the sample solution collecting position, whereby the sample solution (the solution to be analyzed) is collected and guided into the sheath flow cell by the nozzle 43.

The internal structure of the sheath flow cell 47 is the same as is employed in the known flow cytometer, but a reagent injecting chamber similar to that disclosed in JP-A-2-80937 opens at the top of the cell. This allows the nozzle 43 to enter into the inlet 48 of the injecting chamber to dispense the sample solution into the sheath flow cell 47. The sheath solution in a sheath solution tank 6 is pumped up and supplied into the flow cell 47 at a fixed flow rate by a pump 9, the supplied solution flowing down along the inner wall of said flow cell to be discharged into a waste liquid reservoir 95. The sample solution guided into the flow cell flows in the middle of the flow of the sheath solution.

The laser light source 49 is capable of emitting an argon laser beam with an oscillation wavelength of 488 nm. This laser beam flux is widened by a beam expander 50 and then converged by a lens 51 so that it will focus on the flow of the sample solution in the sheath flow cell 47. An objective lens 52 is used for convergence of the fluorescent light from the flow cell 47. A space filter 54 and a wavelength selecting filter 55 are provided in front of a photomultiplier 53 which functions as a photoelectric detector to eliminate scattered light and Raman light. The output of the photomultiplier 53 is first amplified by a preamplifier 18 and then further amplified by a linear amplifier 19, and noise is removed by an infimum pulse-amplitude discriminator 20a and a supremum pulse-amplitude discriminator 20b. Thereafter, the pulse train between the two threshold values is integrated by a counter 56.

A high voltage is applied to the photomultiplier 53 through a transformer 96 and a high-voltage power source 97. The sample numbers, results of counting, calibration curves, histogram of fluorescent determinations, etc., are output to a display 57, a printer 22 and a floppy disc 58. Communication with a personal computer through an interface 59 is also possible.

In operation, when a reaction vessel 34 holding a sample comes to the second reagent pipetting position, a determined amount of the second reagent is sucked up by the nozzle 43 and pipetted into the reaction vessel 34 at the pipetting position. Upon completion of this sequence of operations, the turntable turns counterclockwise through 360° plus one pitch of reaction vessel (one cycle) and comes to a stop. Supposing that the time in which the turntable keeps turning and stays still in one stroke is 20 seconds, a above sequence of operations is repeated with a cycle time of 20 seconds. Thus, in the case of a specific reaction vessel 34 into which the second reagent has been pipetted, its position in a state where the turntable stays still advances counterclockwise by one pitch of reaction vessel upon completion of the above cycle of operations. In the case of this reaction vessel, the first reagent is pipetted at a position in a state where the turntable stays still, for example at a position where the reaction vessel has advanced by one pitch. At this stage, the sample and the first and second reagents have been pipetted into the reaction vessel 34, and consequently the reaction proceeds. Further, when the reaction vessel 34 comes to the fourth reagent pipetting position, a determined amount of the fourth reagent is sucked up by the nozzle 43 and pipetted into the reaction vessel 34 which has reached the pipetting position. When the reaction vessel 34 is transferred to the third reagent pipetting position, a predetermined amount of the third reagent is sucked up by the nozzle 43 and pipetted into the reaction vessel 34 at this pipetting position. This reaction is recorded for a given period of time till discharge of the solution by a discharging means 15 and cleaning by a cleaning device 16, with a cycle time of 20 seconds.

Since the reaction processes for the respective items of a determination in the analysis of nucleic acid are similar to each other, an exemplary analytical operation in a reaction vessel by taking will be made of HBV (B type hepatitis virus). The analytical items are specified by the type of the particle probe added after start of the operation.

In a particle solid phase polynucleotide solution container, there was prepared a latex particle reagent (0.9 µm in diameter) having a single-stranded HBV-DNA probe type 3 fixed thereto. Meanwhile, in a fluorescent particle labelled polynucleotide solution container, there was prepared a fluorescent labelling latex particle reagent having a single-stranded HBV-DNA probe type 1 combined with the fluorescent latex particles (0.1 µm in diameter) containing a coumarin derivative serving as the fluorescent substance. There were also prepared a single-stranded HBV-DNA probe type 2 in the container 90a and a single-stranded HBV-DNA probe type 4 in the container 36a. The probe types were selected so that the single-stranded HBV-DNA probe type 1 and the single-stranded HBV-DNA probe type 2, and the single-stranded HBV-DNA probe type 3 and the single-stranded HBV-DNA probe type 4, would have complementary nucleotide sequences. The single-stranded HBV-DNA probe type 2 and the single-stranded HBV-DNA probe type 4 used here had a complementary nucleotide sequence for the nucleic acid component to be analyzed.

As for the restriction enzyme solution, there was prepared, for example, Hae III as the restriction enzyme which cleaved double-stranded DNA formed by hybridizing the single-stranded HBV-DNA probe type 1 conjugated to the fluorescent labelling latex particles and the single-stranded HBV-DNA probe type 2.

Upon start of the analyzing operation, the single-stranded HBV-DNA probe type 2 was collected from the container 90a while the single-stranded HBV-DNA probe type 4 was collected from the container 36a by the nozzle 43, and both were pipetted into the reaction chamber in the corresponding reaction vessel 34, specifying this reaction vessel as the one for HBV analysis.

Into the thus prepared reaction chamber of the reaction vessel 34 was pipetted the test sample collected from the sample container 33 by the nozzle 43. HBV-DNA in the sample was reacted with the single-stranded HBV-DNA probe type 2 and the single-stranded HBV-DNA probe type 4. This reaction was conducted for 15 minutes.

Then, a determined amount of the latex particle reagent was sucked up from its container on the reagent table 35 by the nozzle 43 and pipetted into the reaction chamber of the corresponding reaction vessel 34.

Further, a determined amount of the fluorescent labelling latex particle reagent was sucked up from its container on the reagent table 35 by the nozzle 43 and supplied into the reaction chamber of the corresponding reaction vessel 34. The reaction was allowed to proceed in the reaction vessel 34 on the turntable at a predetermined temperature (37° C.) for a predetermined period of time (15 minutes). Consequently, the previously obtained hybridized reaction product was further reacted with the single-stranded HBV-DNA probe type 1 and with the single-stranded HBV-DNA probe type 3.

At the reaction solution pipetting position on the turntable 2, a suction pump 3 was disposed beneath the reaction vessel 34. When a reaction vessel 34 was transferred to this position, the reaction solution was pipetted into the filter portion of the reaction vessel 34 by the pipetting nozzle 43. For the filter, there was used a membrane filter having a mesh size of 0.6 μm and a diameter of 10 mm.

At the filter washing position, the operations of injecting the washing fluid into the filter portion of the reaction vessel 34 by the nozzle 43 and actuating the suction device were repeated. Then, with a turn of the reagent table 35, the restriction enzyme solution container 38 was brought to the suction position and a determined amount of the solution containing the restriction enzyme HaeIII 25 in the container 38 was sucked up by the pipetting nozzle 43 and pipetted into the filter portion of the corresponding reaction vessel 34 on the turntable 2. At the filter portion, the double-stranded DNA formed by hybridizing the single-stranded HBV-DNA probe type 1 bound to the fluorescent labelling latex particles and the single-stranded HBV-DNA probe type 2 was cleaved at the predetermined site of cleavage. Consequently, the fluorescent labelling latex particles were suspended in the solution in the reaction vessel 34. The sample solution containing this suspensoid was sucked up by the pipetting nozzle 43 at the sample solution collecting position with the operation of the suction device and introduced into the sheath flow cell 47.

The polynucleotide used here was an oligonucleotide of 30 bases synthesized by the phosphoamidite method using a DNA synthesizer Model 381A supplied by Applied Biosystems Corp.

The second polynucleotide, which is a reagent applicable to the respective analytical items, has a base sequence complementary to both of the sample and the first polynucleotide which is used for all of the analytical items. Therefore, this reagent can be obtained by preparing a polynucleotide having a sequence complementary to the first common polynucleotide, separately synthesizing a polynucleotide having a sequence complementary to the sample corresponding to each of the analytical items, and conjugating them.

Similarly, the fourth polynucleotide, which is a reagent applicable to the respective analytical items, has a base sequence complementary to both of the sample and the third polynucleotide which is used for all of the analytical items. Therefore, this reagent can be obtained by preparing a polynucleotide having a sequence complementary to the third common polynucleotide, separately synthesizing a polynucleotide having a sequence complementary to the sample corresponding to each of the analytical items, and conjugating them.

What is claimed is:

1. A process for detecting the existence of at least two target polynucleotide sequences of oligonucleotide analytes in a nucleic acid sample, comprising the steps of;

(a) mixing said nucleic acid sample with a labeled first common polynucleotide, and a second polynucleotide as a probe which is hybridizable with a first target polynucleotide sequence of oligonucleotide and with the labeled first common polynucleotide, to detect the existence of the first target polynucleotide sequence of oligonucleotide; and (b) mixing said nucleic acid sample with the labeled first common polynucleotide used in step (a) for detecting said first target polynucleotide sequence of oligonucleotide, and a third polynucleotide as a probe which is hybridizable with a second target polynucleotide sequence of oligonucleotide and with the labeled first common polynucleotide, to detect the existence of the second target polynucleotide sequence of oligonucleotide.

2. A process according to claim 1, which further comprises a step of (c) cleaving or dissociating a double-stranded portion formed by the labeled first common polynucleotide and the third polynucleotide, by the action of a restriction enzyme recognizing said portion, and a step of (d) detecting a signal derived from a label liberated by the cleavage.

3. A process for detecting the existence of at least two target polynucleotide sequences of oligonucleotide analytes in a nucleic acid sample, comprising the steps of:

(a) mixing said nucleic acid sample with a labeled first common polynucleotide, a second polynucleotide as a probe which is hybridizable with a first target polynucleotide sequence of oligonucleotide and with the labeled first common polynucleotide, a third common polynucleotide attached to a solid phase and which is selected without regard to said first target polynucleotide sequence of oligonucleotide, and a fourth polynucleotide as a probe which is hybridizable with said first target polynucleotide sequence of oligonucleotide and with the third common polynucleotide attached to the solid phase, to detect the existence of the first target polynucleotide sequence of oligonucleotide; and (b) mixing said nucleic acid sample with the labeled first common polynucleotide used in step (a) for detecting said first target polynucleotide sequence of oligonucleotide, a fifth polynucleotide as a probe which is hybridizable with a second target polynucleotide sequence of oligonucleotide and with the labeled first common polynucleotide, the third common polynucleotide attached to the solid phase and used in step (a), and a sixth polynucleotide as a probe which is hybridizable with said second target polynucleotide sequence of oligonucleotide and with the third common polynucleotide attached to the solid phase, to detect the existence of the second target polynucleotide sequence of oligonucleotide.

4. A process according to claim 3, which further comprises a step of (c) cleaving or dissociating a double-stranded portion formed by the labeled first common polynucleotide and the fifth polynucleotide, by the action of a restriction enzyme recognizing said portion, and a step of (d) detecting a signal derived from a label liberated by the cleavage.

5. A process according to claim 3, which further comprises a step of (c) cleaving or dissociating a double-stranded portion formed by the third common polynucleotide and the sixth polynucleotide, by the action of a restriction enzyme recognizing said portion, and a step of (d) detecting a signal derived from a label liberated by the cleavage.

6. A process according to claim 1, which further comprises a step of (c) cleaving or dissociating a double-stranded portion formed by the labeled first common polynucleotide and the second polynucleotide, by the action of a restriction enzyme recognizing said portion, and a step of (d) detecting a signal derived from a label liberated by the cleavage.

7. A process according to claim 3, which further comprises a step of (c) cleaving or dissociating a double-stranded portion formed by the labeled first common polynucleotide and the second polynucleotide, by the action of a restriction enzyme recognizing said portion, and a step of (d) detecting a signal derived from a label liberated by the cleavage.

8. A process according to claim 3, which further comprises a step of (c) cleaving or dissociating a double-stranded portion formed by the third common polynucleotide and the fourth polynucleotide, by the action of a restriction enzyme recognizing said portion, and a step of (d) detecting a signal derived from a label liberated by the cleavage.

9. A process according to claim 1, wherein the labeled first common polynucleotide is labeled with particles by which the labeled first common polynucleotide is distinguished for detection of a target polynucleotide sequence of oligonucleotide hybridized thereto.

10. A process according to claim 2, wherein the labeled first common polynucleotide is labeled with particles by which the labeled first common polynucleotide is distinguished for detection of a target polynucleotide sequence of oligonucleotide hybridized thereto.

11. A process according to claim 3, wherein the labeled first common polynucleotide is labeled with particles by which the labeled first common polynucleotide is distinguished for detection of a target polynucleotide sequence of oligonucleotide hybridized thereto.

12. A process according to claim 4, wherein the labeled first common polynucleotide is labeled with particles by which the labeled first common polynucleotide is distinguished for detection of a target polynucleotide sequence of oligonucleotide hybridized thereto.

13. A process according to claim 5, wherein the labeled first common polynucleotide is labeled with particles by which the labeled first common polynucleotide is distinguished for detection of a target polynucleotide sequence of oligonucleotide hybridized thereto.

* * * * *